: # (12) United States Patent
Falk et al.

(10) Patent No.: US 8,198,361 B2
(45) Date of Patent: *Jun. 12, 2012

(54) SILICON POLYETHERS AND A METHOD OF PRODUCING THE SAME

(75) Inventors: Benjamin Falk, Yorktown Heights, NY (US); Kalman Koczo, Suffern, NY (US); Antonio Palumbo, Siracusa (IT)

(73) Assignee: Momentive Performance Materials Inc., Albany, NY (US)

( * ) Notice: Subject to any disclaimer, the term of this patent is extended or adjusted under 35 U.S.C. 154(b) by 46 days.

This patent is subject to a terminal disclaimer.

(21) Appl. No.: 12/694,636

(22) Filed: Jan. 27, 2010

(65) Prior Publication Data

US 2011/0184106 A1    Jul. 28, 2011

(51) Int. Cl.
*C08L 83/00* (2006.01)
*C08L 83/04* (2006.01)
*C07F 7/02* (2006.01)

(52) U.S. Cl. ......... 524/588; 525/474; 556/450; 556/453

(58) Field of Classification Search .................. 525/474
See application file for complete search history.

(56) References Cited

U.S. PATENT DOCUMENTS

| | | | | |
|---|---|---|---|---|
| 3,700,400 A * | 10/1972 | Cuthbertson | ...................... | 8/499 |
| 5,004,559 A * | 4/1991 | Koerner et al. | ................ | 516/144 |
| 5,356,633 A * | 10/1994 | Woodle et al. | ................. | 424/450 |
| 5,981,613 A * | 11/1999 | Cobb et al. | ..................... | 521/112 |
| 5,985,948 A * | 11/1999 | Burkhart et al. | ............... | 521/112 |
| 6,207,717 B1 * | 3/2001 | Lin et al. | ..................... | 514/772.1 |
| 6,291,622 B1 * | 9/2001 | Drose et al. | ...................... | 528/31 |
| 6,642,309 B2 * | 11/2003 | Komitsu et al. | ............... | 525/100 |
| 6,897,280 B2 * | 5/2005 | Heisler et al. | ................... | 528/15 |
| 2001/0004646 A1 * | 6/2001 | Burkhart et al. | ............... | 521/110 |
| 2008/0262143 A1 * | 10/2008 | Sato et al. | ...................... | 524/547 |

FOREIGN PATENT DOCUMENTS

EP                822218         2/1998

\* cited by examiner

*Primary Examiner* — Robert S Loewe
(74) *Attorney, Agent, or Firm* — Dominick G. Vicari

(57) ABSTRACT

The present invention provides a non-crosslinked silicon polyether composition comprising at least one compound with the following formula;

$$[(R^1O)(C_2H_4O)_a(C_3H_6O)_b(C_4H_8O)_c]_d R^2(R^3)_e$$

wherein $R^1$ is a monovalent radical defined as $$M_g M^A_h M^B_i M^H_j M^E_k D_l D^H_m D^E_n T_o T^H_p T^E_q Q_r$$

$M=R^4R^5R^6SiO_{1/2}$; $M^A=R^7R^8R^9SiR^{10}$; $M^B=[(R^{11}R^{12}R^{13}Si)_s R^{14}]_t Si(R^{15})_u(R^{16})_v R^{17}$; $M^H=R^{18}Si(R^{19})(R^{20})O_{1/2}$; $M^E=R^{21}R^{22}R^ESiO_{1/2}$; $D=R^{23}R^{24}SiO_{2/2}$; $D^H=R^{25}Si(R^{26})O_{2/2}$; $D^E=R^{27}R^ESiO_{2/2}$; $T=R^{28}SiO_{3/2}$; $T^H=R^{29}SiO_{3/2}$; $T^E=R^ESiO_{2/2}$; and $Q=SiO_{4/2}$; $R^2$ and $R^{14}$ are polyvalent linear or branched; $R^3$ is $—(C_2H_4O)(C_3H_6O)_b(C_4H_8O)_c—R^{30}$ or $R^1$; $R^{30}$ is a monovalent saturated; $R^4$, $R^5$, $R^6$, $R^7$, $R^8$, $R^9$, $R^{11}$, $R^{12}$, $R^{13}$, $R^{15}$, $R^{16}$, $R^{19}$, $R^{20}$, $R^{21}$, $R^{22}$, $R^{23}$, $R^{24}$, $R^{26}$, $R^{27}$, and, $R^{28}$ are monovalent hydrocarbon radicals having from 1 to about 10 carbons; $R^{10}$, $R^{17}$, $R^{18}$, $R^{25}$ and $R^{29}$ are divalent hydrocarbon radicals having 1 to about 25 carbons; $R^E$ is $—R^{32}—(C_2H_4O)_a(C_3H_6O)_b(C_4H_8O)_c—R^{33}$; $R^{32}$ is a divalent hydrocarbon radical having 1 to about 60 carbons; $R^{33}$ is a monovalent hydrocarbon radical having 1 to about 20 carbons; h is 0 or 1 subject to the limitation if h is 1 then $g+i+j+k+l+m+n+o+p+q+r=0$; subscript d is $1 < d+e \leq$ about 25 limitation that the sum d+e is equal to the valency of $R^2$ and $1 < d$; e is zero; subscripts a, b and c are zero or positive; subscripts g, h, i, j, k, l, m, n, o, p, q and r are zero or positive; subscript s is positive; and subscripts t, u, and v are zero or positive.

8 Claims, No Drawings

SILICON POLYETHERS AND A METHOD OF PRODUCING THE SAME

FIELD OF THE INVENTION

The present invention relates to branched, non-crosslinked silicon polyether based compositions and processes for their preparation.

BACKGROUND OF THE INVENTION

Modified silicones can exhibit a variety of physical properties. The polymers can be modified to be hydrophilic, lipophilic and hydrophobic depending on the nature of the organic substituents. Recently, branched, non-crosslinked organo-modified polysiloxane compositions comprising multiple siloxane chains bonded to a core via covalent bonds have been produced and identified by the present invention as having improved demulsification properties.

The branched organo-modified polysiloxane compositions and their preparation are further described in the sections below.

SUMMARY OF THE INVENTION

According to the invention, there is provided a non-crosslinked silicon polyether composition comprising at least one compound with the following formula;

$$[(R^1O)(C_2H_4O)_a(C_3H_6O)_b(C_4H_8O)_c]_dR^2(R^3)_e$$

whereas
$R^1$ is a monovalent radical defined as $$M_gM^A{}_hM^B{}_iM^H{}_jM^E{}_kD_lD^H{}_mD^E{}_nT_oT^H{}_pT^E{}_qQ_r$$

with
$M = R^4R^5R^6SiO_{1/2}$;
$M^A = R^7R^8R^9SiR^{10}$;
$M^B = [(R^{11}R^{12}R^{13}Si)_sR^{14}]_tSi(R^{15})_u(R^{16})_vR^{17}$;
$M^H = R^{18}Si(R^{19})(R^{20})O_{1/2}$;
$M^E = R^{21}R^{22}R^ESiO_{1/2}$;
$D = R^{23}R^{24}SiO_{2/2}$;
$D^H = R^{25}Si(R^{26})O_{2/2}$;
$D^E = R^{27}R^ESiO_{2/2}$;
$T = R^{28}SiO_{3/2}$;
$T^H = R^{29}SiO_{3/2}$;
$T^E = R^ESiO_{2/2}$; and
$Q = SiO_{4/2}$;
where $R^2$ and $R^{14}$ are polyvalent linear or branched unsaturated or saturated hydrocarbon radicals optionally containing heteroatoms and hydroxyl groups subject to the limitation that the valency of $R^2$ and $R^{14}$ is at least two and they contain less than about 25 carbon atoms;
$R^3$ is $-(C_2H_4O)_{aa}(C_3H_6O)_{bb}(C_4H_8O)_{cc}-R^{30}$ or $R^1$;
$R^{30}$ is a monovalent saturated or unsaturated hydrocarbon radical having from 1 to about 20 carbon atoms;
$R_4, R^5, R^6, R^7, R^8, R^9, R^{11}, R^{12}, R^{13}, R^{15}, R^{16}, R^{19}, R^{20}, R^{21}, R^{22}, R^{23}, R^{24}, R^{26}, R^{27}$, and, $R^{28}$ are each independently selected from the group of monovalent hydrocarbon radicals having from 1 to about 10 carbon atoms or $OR^{31}$;
$R^{31}$ is a monovalent hydrocarbon radical that optionally contains heteroatoms having 1 to about 10 carbon atoms;
$R^{10}, R^{17}, R^{18}, R^{25}$ and $R^{29}$ are independently selected from the group of divalent hydrocarbon radicals having 1 to about 25 carbon atoms;
$R^E$ is $-R^{32}-(C_2H_4O)_a(C_3H_6O)_b(C_4H_8O)_c-R^{33}$;
$R^{32}$ is a divalent hydrocarbon radical having from 1 to about 60 carbon atoms;
$R^{33}$ is a monovalent saturated or unsaturated hydrocarbon radical having from 1 to about 20 carbon atoms;
subscript h is 0 or 1 subject to the limitation if h is 1 then g+i+j+k+l+m+n+o+p+q+r=0;
subscript d is positive subject to the limitation 2<d+e≦about 25 subject to the limitation that the sum d+e is equal to the valency of $R^2$ and 1<d;
subscript e is zero or up to about 24;
subscripts a, b and c are zero or positive subject to the limitation 0<a+b+c≦about 300;
subscripts aa, bb and cc are zero or positive subject to the limitation 0<aa+bb+cc≦about 300;
subscripts g, h, i, j, k, l, m, n, o, p, q and r each are zero or positive and have values ranging from about 0 to about 300;
subscript s is positive subject to the limitation 0<s<25 and s is equal to the valency of $R^{14}-1$; and
subscripts t, u, and v are zero or positive subject to the limitations 1≦t and t+u+v=3.

The present invention is also directed to methods for producing the non-crosslinked silicon polyether compositions of the present invention.

Additional embodiments are also part of the present invention, which are further described in the Detailed Description of the Invention below.

DETAILED DESCRIPTION OF THE INVENTION

According to the invention, there is provided a non-crosslinked silicon polyether composition comprising at least one compound with the following formula;

$$[(R^1O)(C_2H_4O)_a(C_3H_6O)_b(C_4H_8O)_c]_dR^2(R^3)_e$$

whereas
$R^1$ is a monovalent radical defined as $$M_gM^A{}_hM^B{}_iM^H{}_jM^E{}_kD_lD^H{}_mD^E{}_nT_oT^H{}_pT^E{}_qQ_r$$

wherein
$M = R^4R^5R^6SiO_{1/2}$;
$M^A = R^7R^8R^9SiR^{10}$;
$M^B = [(R^{11}R^{12}R^{13}Si)_sR^{14}]_tSi(R^{15})_u(R^{16})_vR^{17}$;
$M^H = R^{18}Si(R^{19})(R^{20})O_{1/2}$;
$M^E = R^{21}R^{22}R^ESiO_{1/2}$;
$D = R^{23}R^{24}SiO_{2/2}$;
$D^H = R^{25}Si(R^{26})O_{2/2}$;
$D^E = R^{27}R^ESiO_{2/2}$;
$T = R^{28}SiO_{3/2}$;
$T^H = R^{29}SiO_{3/2}$;
$T^E = R^ESiO_{2/2}$; and
$Q = SiO_{4/2}$;
where $R^2$ and $R^{14}$ are polyvalent linear or branched unsaturated or saturated hydrocarbon radicals optionally containing heteroatoms and hydroxyl groups subject to the limitation that the valency of $R^2$ and $R^{14}$ is at least two and they contain less than about 25 carbon atoms, preferably at least one and less than about 20 carbon atoms, and more preferably at least one and less than about 15 carbon atoms;
$R^3$ is $-(C_2H_4O)_{aa}(C_3H_6O)_{bb}(C_4H_8O)_{cc}-R^{30}$ or $R^1$;
$R^{30}$ is a monovalent saturated or unsaturated hydrocarbon radical having from 1 to about 20 carbon atoms, preferably from 1 to about 10 carbon atoms and more preferably from 1 to about 5 carbon atoms;
$R_4, R^5, R^6, R^7, R^8, R^9, R^{11}, R^{12}, R^{13}, R^{15}, R^{16}, R^{19}, R^{20}, R^{21}, R^{22}, R^{23}, R^{24}, R^{26}, R^{27}$, and, $R^{28}$ are each independently selected from the group of monovalent hydrocarbon radicals having from 1 to about 10 carbon atoms, preferably from 1 to about 5 carbon atoms and more preferably from 1 to about 3 carbon atoms or $OR^{31}$;

$R^{31}$ is a monovalent hydrocarbon radical that optionally contains heteroatoms having 1 to about 10 carbon atoms;

$R^{10}$, $R^{17}$, $R^{18}$, $R^{25}$ and $R^{29}$ are independently selected from the group of divalent hydrocarbon radicals having 1 to about 25 carbon atoms, preferably from 2 to about 20 carbon atoms and more preferably from 3 to about 10 carbon atoms;

$R^E$ is $-R^{32}-(C_2H_4O)_a(C_3H_6O)_b(C_4H_8O)_c-R^{33}$;

$R^{32}$ is a divalent hydrocarbon radical having from 1 to about 60 carbon atoms, preferably from 2 to about 20 carbon atoms and more preferably from 3 to about 10 carbon atoms;

$R^{33}$ is a monovalent saturated or unsaturated hydrocarbon radical having from 1 to about 20 carbon atoms, preferably from 1 to about 10 carbon atoms and more preferably from 1 to about 5 carbon atoms;

subscript h is 0 or 1 subject to the limitation if h is 1 then g+i+j+k+l+m+n+o+p+q+r=0;

subscript d is positive subject to the limitation $2<d+e\leq$about 25 subject to the limitation that the sum d+e is equal to the valency of $R^2$ and $1<d$;

subscript e is zero or up to about 24;

subscripts a, b and c are zero or positive subject to the limitation $0<a+b+c\leq$about 300, preferably $0<a+b+c\leq$about 250 and more preferably $1<a+b+c\leq$about 200;

subscripts aa, bb and cc are zero or positive subject to the limitation $0<aa+bb+cc\leq$about 300, preferably $0<aa+bb+cc\leq$about 250 and more preferably $1<aa+bb+cc\leq$about 200;

the subscripts g, h, i, j, k, l, m, n, o, p, q and r are zero or positive and have values ranging from about 0 to about 300;

subscript s is positive subject to the limitation $0<s<25$, preferably $0<s<20$ and more preferably $0<s<10$ and s is equal the valency of $R^{14}-1$; and subscripts t, u, and v are zero or positive subject to the limitations $1\leq t$ and $t+u+v=3$.

The present invention is directed to a non-crosslinked silicon polyether composition comprising the compound having the following formula;

$$[(R^1O)(C_2H_4O)_a(C_3H_6O)_b(C_4H_8O)_c]_dR^2(R^3)_e$$

whereas $R^1$ is $(CH_3)_3SiOSi(R^{25})(CH_3)OSi(C_3)_3$;

$R^{25}$ is a divalent hydrocarbon with about 3 to about 10 carbon atoms;

subscript a is about 5 to about 50;

subscript b is about 5 to about 50;

subscripts c and e are 0;

subscript d is about 3;

$R^2$ is a trivalent hydrocarbon with about 3 to about 10 carbon atoms.

According to still another aspect of the present invention is directed to a non-crosslinked silicon polyether composition comprising the compound having the following formula;

$$[(R^1O)(C_2H_4O)_a(C_3H_6O)_b(C_4H_8O)_c]_dR^2(R^3)_e$$

wheereas $R^1$ is $(CH_3)_3SiOSi(R^{25})(CH_3)OSi(C_3)_3$;

$R^{25}$ is a divalent hydrocarbon with about 3 to about 10 carbon atoms;

subscript a and d are about 4;

subscript b, c and e are 0;

$R^2$ is a tetravalent hydrocarbon with about 4 to about 20 carbon atoms.

According to still another aspect of the present invention is directed to a non-crosslinked silicon polyether composition comprising the compound having the following formula;

$$[(R^1O)(C_2H_4O)_a(C_3H_6O)_b(C_4H_8O)_c]_dR^2(R^3)_e$$

whereas $R^1$ and $R^3$ are $(CH_3)_3SiCH_2CH_2Si(CH_3)_2)R^{17}-$;

$R^{17}$ is a divalent hydrocarbon with about 3 to about 10 carbon atoms;

subscript a is about 5 to about 50;

subscript b is about 0 to about 10;

subscript c is 0;

$R^2$ is $CH_3CH_2C(CH_2-)_2(CH_2O-)$ where $R^3$ is connected to the O atom in $R^2$;

subscript d is about 2;

subscript e is about 1.

According to still another aspect of the present invention is directed to a non-crosslinked silicon polyether composition comprising the compound having the following formula;

$$[(R^1O)(C_2H_4O)_a(C_3H_6O)_b(C_4H_8O)_c]_dR^2(R^3)_e$$

whereas $R^1$ and $R^3$ are $(CH_3)_3SiOSi(R^{25})(CH_3)OSi(CH_3)_3$;

$R^{25}$ is a divalent hydrocarbon with about 3 to about 10 carbon atoms;

subscript a is about 5 to about 50;

subscript d is 2;

subscript e is 1;

subscripts b and c are 0;

$R^2$ is $CH_3CH_2C(CH_2-)_2(CH_2O-)$ where $R^3$ is connected to the O atom in $R^2$.

In the specification and claims herein, the following terms and expressions are to be understood as indicated.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "cross-linked polymers" means polymer molecules which are built from monomers which are linked together at many points other than their ends and as a result molecules with large size form and the material is non-pourable solid or gel-like which cannot be dissolved in any solvent.

The copolymers in our invention are "non-crosslinked", which means that their monomers are either not linked together at points other than their ends or the linkages between the polymers are so few that the copolymer is either liquid or can be dissolved in at least one solvent.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

Other optional ingredients may be added in the compositions of the present invention including coupling agents, e.g., awe coupling agents, curing aids, e.g., including activators, retarders and accelerators, processing additives such as oils, plasticizers, tackifying resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and such selection is within the knowledge of one of skill in the art, as are the required amounts of such additives known to one of skill in the art.

The compositions of the present invention can be used commercially as a demulsifying agents, in agricultural compositions including fertilizers, in cosmetics and personal care products, in household cleaners, in coating compositions such as waxes and the like, in water processing apparatuses as well as other products.

SYNTHETIC EXAMPLES

Preparation Example A

A polyether with the average structure of $CH_2=C(CH_3)CH_2O(CH_2CH_2O)_9CH_2C(CH_3)=CH_2$ (150.00 g), sodium propionate (0.15 g), and toluene (70.0 g) were added to a round bottom flask equipped with a Dean-Starke trap filled with toluene, an overhead stirrer, heating mantel and thermocouple. The material was brought to reflux for 2 hrs thus drying the polyether. The reactor was cooled and the Dean-Starke trap was replaced with a condenser. 1,1,1,3,5,5,5-heptamethyltrisiloxane (125.19 g) was added and the reaction was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 8.4 torr and held for 2 hrs. The product was then pressure filtered through a 5 micron filter pad. The product was liquid with a viscosity of 47.7 cP and exhibited an amber color.

Preparation Example B

A polyether with the average structure of $CH_2=C(CH_3)CH_2O(CH_2CH_2O)_{24}(CH2CH(CH3)O)_6CH2C(CH_3)=CH_2$ (150.00 g) and sodium propionate (0.15 g) were added to a round bottom flask equipped with a condenser, an overhead stirrer, heating mantel and thermocouple. 1,1,1,3,5,5,5-heptamethyltrisiloxane (27.90 g) was added and the reaction was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 10 torr and held for 2 hrs. Diatomaceous earth, Celite 545 (10 g) was added to the product then pressure filtered through a 5 micron filter pad. The product was liquid with a viscosity of 951.0 cP and exhibited a brown yellow color.

Preparation Example C

A polyether with the average structure of $CH_2=C(CH_3)CH_2O(CH_2CH_2O)_{22.7}(CH2CH(CH3)=CH2C(CH_3)=CH_2$(100.00 g), sodium propionate (0.15 g), and isopropanol (20.0 g) were added to a round bottom flask equipped with a condenser, an overhead stirrer, heating mantel and thermocouple. 1,1,1,3,5,5,5-heptamethyltrisiloxane (44.06 g) was added and the reaction was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 10 torr and held for 2 hrs. Diatomaceous earth, Celite 545 (10 g) was added to the product then pressure filtered through a 5 micron filter pad. The product solidified upon standing and exhibited a brown yellow color.

Preparation example D

Trismethallyl capped ethoxylated trimethylolpropane with an average molecular weight of 1000 g/mol (150 g), sodium propionate (0.15 g), and 1,1,1,3,5,5,5-heptamethyltrisiloxane (67.92 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 9.8 torr and held for 2 hrs. Diatomaceous earth, Celite 545 (5 g) was added to the product then pressure filtered through a 5 micron filter pad. The product was liquid with a viscosity of 165.3 cP and exhibited a clear amber color.

Preparation example E

Trismethallyl capped alkoxylated (14.6 EO and 4.2 PO) glycerol with an average molecular weight of 1000 g/mol (150 g), sodium propionate (0.15 g), and 1,1,1,3,5,5,5-heptamethyltrisiloxane (62.04 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 8.8 torr and held for 2 hrs. Diatomaceous earth, Celite 545 (5 g) was added to the product then pressure filtered through a 5 micron filter pad. The product was liquid with a viscosity of 137.4 cP and exhibited a clear amber color.

Preparation example F

Trismethallyl capped alkoxylated (58.3 EO and 10.5 PO) glycerol with an average molecular weight of 3600 g/mol (150 g), sodium propionate (0.15 g), and 1,1,1,3,5,5,5-heptamethyltrisiloxane (27.17 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 9.2 torr and held for 2 hrs. Diatomaceous earth, Celite 545 (5 g) was added to the product then pressure filtered through a 5 micron filter pad. The product was liquid with a viscosity of 856.5 cP and exhibited a dark brown color.

Preparation example G

Trismethallyl capped alkoxylated (68.7 EO and 25.6 PO) glycerol with an average molecular weight of 4900 g/mol (150 g), sodium propionate (0.15 g), and 1,1,1,3,5,5,5-heptamethyltrisiloxane (19.46 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 9.2 torr and held for 2 hrs. Diatomaceous earth, Celite 545 (5 g) was added to the product then pressure filtered through a 5 micron filter pad. The product was liquid with a viscosity of 1171.0 cP and exhibited a clear amber color.

Preparation example H

Trismethallyl capped alkoxylated (15.8 EO and 2.4 PO) glycerol with an average molecular weight of 1000 g/mol (150 g), sodium propionate (0.15 g), and 1,1,1,3,5,5,5-heptamethyltrisiloxane (93.62 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 15.0 torr and held for 2 hrs. Diatomaceous earth, Celite 545 (5 g) was added to the product then pressure filtered through a 5 micron filter pad. The product was liquid with a viscosity of 136.5 cP and exhibited a clear amber color.

Preparation example I

Trismethallyl capped ethoxylated (50 EO) glycerol with an average molecular weight of 2300 g/mol (76.9 g), sodium propionate (0.05 g), and 1,1,1,3,5,5,5-heptamethyltrisiloxane (23.1 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 15.0 torr and held for 2 hrs. Diatomaceous earth, Celite 545 (5 g) was added to the product then pressure filtered through a 5 micron filter pad. The product was solidified upon standing and exhibited a clear light amber color.

Preparation example J

Trismethallyl capped ethoxylated (20 EO) glycerol with an average molecular weight of 1000 g/mol (60.6 g), sodium propionate (0.05 g), and 1,1,1,3,5,5,5-heptamethyltrisiloxane (39.4 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 15.0 torr and held for 2 hrs. Diatomaceous earth, Celite 545 (5 g) was added to the product then pressure filtered through a 5 micron filter pad. The product was a liquid with a viscosity of 128.4 cP and exhibited a clear light amber color.

Preparation example K

Trismethallyl capped ethoxylated (20 EO) trimethylolpropane with an average molecular weight of 1200 g/mol (61.4 g), sodium propionate (0.05 g), and 1,1,1,3,5,5,5-heptamethyltrisiloxane (38.6 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 15.0 torr and held for 2 hrs. Diatomaceous earth, Celite 545 (5 g) was added to the product then pressure filtered through a 5 micron filter pad. The product was a liquid with a viscosity of 163.2 cP and exhibited a clear light amber color.

Preparation example L

Tetramethallyl capped ethoxylated (15 EO) penthaerithrytol with an average molecular weight of 800 g/mol (150.0 g), sodium propionate (0.15 g), and 1,1,1,3,5,5,5-heptamethyltrisiloxane (125.92 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 12.0 torr and held for 2 hrs. Diatomaceous earth, Celite 545 (5 g) was added to the product then pressure filtered through a 5 micron filter pad. The product was a liquid with a viscosity of 99.6 cP and exhibited a clear light amber color.

Preparation example M

Bismethallyl capped ethoxylated (50 EO) trimethylolpropane monoallyl ether with an average molecular weight of 2400 g/mol (150.0 g), sodium propionate (0.15 g), and 1,1,1,3,5,5,5-heptamethyltrisiloxane (44.42 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 10.0 torr and held for 2 hrs. Diatomaceous earth, Celite 545 (5 g) was added to the product then pressure filtered through a 5 micron filter pad. The product solidified upon standing and exhibited a clear light amber color.

Preparation example N

Bismethallyl capped ethoxylated (20 EO) trimethylolpropane monoallyl ether with an average molecular weight of 1050 g/mol (150.0 g), sodium propionate (0.15 g), and 1,1,1,3,5,5,5-heptamethyltrisiloxane (95.45 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 12.0 torr and held for 2 hrs. Diatomaceous earth, Celite 545 (5 g) was added to the product then pressure filtered through a 5 micron filter pad. The product was a liquid with a viscosity of 163 cP and exhibited a clear light amber color.

Preparation example O

Bismethallyl capped ethoxylated (20 EO) trimethylolpropane monoallyl ether with an average molecular weight of 1050 g/mol (200.0 g), sodium propionate (0.15 g), and 1-trimethylsilyl-2-dimethylsilylethane (95.4 g) were added to a round bottom flask equipped with a condenser, an overhead stirrer, heating mantel and thermocouple. The reaction medium was heated to 85° C. Karstedt's catalyst (25 ppm Pt) was added and the reaction medium was stirred for 16 hrs. An infrared spectrum was taken to insure completion of the reaction. The product was transferred to a single neck flask and placed on a rotary evaporator in an oil bath at 120° C. Using a nitrogen sparge the flask was evacuated to 12.0 torr and held for 2 hrs. Diatomaceous earth, Celite 545 (5 g) was added to the product then pressure filtered through a 5 micron filter pad. The product was a liquid and exhibited a clear light amber color.

Preparation example P

Bismethallyl capped ethoxylated (20 EO) trimethylolpropane monoallyl ether with an average molecular weight of 1050 g/mol (100.0 g) and sodium propionate (0.10 g) were added to a round bottom flask equipped with a dry ice condenser, an overhead stirrer, heating mantel and thermocouple. The reaction medium was heated to 85° C. Karstedt's catalyst (25 ppm Pt) was added and trimethylsilane (22.1 g) was bubbled under the surface of the reaction medium. Once all the silane was added the reaction medium was stirred for an additional 16 hrs. An infrared spectrum was taken to insure completion of the reaction. The product was transferred to a single neck flask and placed on a rotary evaporator in an oil bath at 120° C. Using a nitrogen sparge the flask was evacuated to 12.0 torr and held for 2 hrs. Diatomaceous earth, Celite 545 (5 g) was added to the product then pressure filtered through a 5 micron filter pad. The product was a liquid and exhibited a clear light amber color.

It is understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

What is claimed is:

1. A non-crosslinked silicon polyether composition comprising at least one compound with the following formula;

$$[(R^1O)(C_2H_4O)_a(C_3H_6O)_b(C_4H_8O)_c]_dR^2(R^3)_e$$

whereas $R^1$ is a monovalent radical difined as $$M_gM^A_hM^B_iM^H_jM^E_kD_lD^H_mD^E_nT_oT^H_pT^E_qQ_r.$$

wherein
$M=R^4R^5R^6SiO_{1/2}$;
$M^A=R^7R^8R^9SiR^{10}$;
$M^B=[(R^{11}R^{12}R^{13}Si)_sR^{14}]_rSi(R^{15})_u(R^{16})_vR^{17}$
$M^H=R^{18}Si(R^{19})(R^{20})O_{1/2}$;
$M^E=R^{21}R^{22}R^ESiO_{1/2}$;
$D=R^{23}R^{24}SiO_{2/2}$;
$D^H=R^{25}Si(R^{26})O_{2/2}$;
$D^E=R^{27}R^ESiO_{2/2}$;
$T=R^{28}SiO_{3/2}$;
$T^H-R^{29}SiO_{3/2}$;
$T^E=R^ESiO_{2/2}$; and
$Q=SiO_{4/2}$;
where $R^2$ and $R^{14}$ are polyvalent linear or branched unsaturated or saturated hydrocarbon radicals optionally containing heteroatoms and hydroxyl groups subject to the limitation that the valency of $R^2$ and $R^{14}$ is at least two and contains from 1 to about 25 carbon atoms;

$R^3$ is $-(C_2H_4O)_a(C_3H_6O)_b(C_4H_8O)_c-R^{30}$ or $R^1$;

$R^{30}$ is a monovalent saturated or unsaturated hydrocarbon radical having from 1 to about 20 carbon atoms;

$R^4, R^5, R^6, R^{11}, R^{12}, R^{13}, R^{15}, R^{16}, R^{19}, R^{20}, R^{21}, R^{22}, R^{23}, R^{24}, R^{26}, R^{27}$, and, $R^{28}$ are each independently selected from the group of monovalent hydrocarbon radicals having from 1 to about 10 carbon atoms or $OR^{31}$, and $R^7, R^8$ and $R^9$ are each independently selected from the group of monovalent hydrocarbon radicals having from 1 to about 10 carbon atoms;

$R^{31}$ is a monovalent hydrocarbon radical that optionally contains heteroatoms having 1 to about 10 carbon atoms;

$R_{10}, R_{17}, R_{18}, R_{25}$ and $R^{29}$ are independently selected from the group of divalent hydrocarbon radicals having 1 to about 25 carbon atoms;

$R^E$ is $-R^{32}-(C_2H_4O)_a(C_3H_6O)_b(C_4H_8O)_c-R^{33}$;

$R^{32}$ is a divalent hydrocarbon radical having from 1 to about 60 carbon atoms;

$R^{33}$ is a monovalent saturated or unsaturated hydrocarbon radical having from 1 to about 20 carbon atoms;

subscript h is 0 or 1 subject to the limitation if h is 1 then g+i+j+k+l+m+n+o+p+q+r=0;

subscript d is positive subject to the limitation $2 \leq d \leq$ about 25 subject to the limitation that the sum d+e is equal to the valency of $R^2$;

subscript e is zero or up to about 24;

subscripts a, b and c are zero or positive subject to the limitation $0 < a+b+c \leq$ about 300;

the subscripts g, i, j, k, l, m, n, o, p, q and r are zero or positive and have values ranging from about 0 to about 300;

subscript s is positive subject to the limitation $0 < s < 25$ and s is equal to the valency of $R^{14}$ minus 1;

subscripts t, u, and v are zero or positive subject to the limitations $1 \leq t$ and t+u+v=3; and, at least one of the subscripts i, i, m or p are positive or h is one.

2. The non-crosslinked silicon polyether composition of claim 1 wherein said non-crosslinked silicon polyether composition comprises the compound having the following formula;

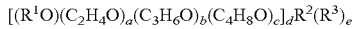

wherein $R^1$ is $(CH_3)_3SiOSi(R^{25})(CH_3)OSi(CH_3)_3$;

$R^{25}$ is $-CH_2CH(H$ or $CH_3)CH_2-$ subscript a is about 5 to about 50;

subscript b is about 5 to about 50;

subscripts c and e are 0;

subscript d is about 3; and $R^2$ is a trivalent hydrocarbon with about 3 to about 10 carbon atoms.

3. The non-crosslinked silicon polyether composition of claim 1 wherein said non-crosslinked silicon polyether composition comprises the compound having the following formula;

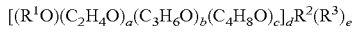

wherein $R^1$ is $(CH_3)_3SiOSi(R^{25})(CH_3)OSi(CH_3)_3$;

$R^{25}$ is a divalent hydrocarbon with about 3 to about 10 carbon atoms;

subscripts a and d are each about 4;

subscripts b, c and e are 0; and $R^2$ is a tetravalent hydrocarbon with about 4 to about 20 carbon atoms.

4. The non-crosslinked silicon polyether composition of claim 1 wherein said non-crosslinked silicon polyether composition comprises the compound having the following formula;

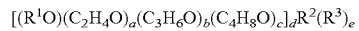

wherein $R^1$ and $R^3$ are $(CH_3)_3SiCH_2CH_2Si(CH_3)_2)R^{17}-$;

$R^{17}$ is a divalent hydrocarbon with about 3 to about 10 carbon atoms;

subscript a is about 5 to about 50;

subscript b is about 0 to about 10;

subscript c is 0;

$R^2$ is $CH_3CH_2C(CH_2-)_2(CH_2O-)$ where $R^3$ is connected to the O atom in $R^2$;

subscript d is about 2; and subscript e is about 1.

5. The non-crosslinked silicon polyether composition of claim 1 wherein said non-crosslinked silicon polyether composition comprises the compound having the following formula;

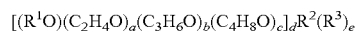

wherein $R^1$ and $R^3$ are $(CH_3)_3SiOSi(R^{25})(CH_3)OSi(CH_3)_3$;

$R^{25}$ is a divalent hydrocarbon with about 3 to about 10 carbon atoms;

subscript a is about 5 to about 50;

subscript d is 2;

subscript e is 1;

subscripts b and c are 0; and $R^2$ is $CH_3CH_2C(CH_2-)_2(CH_2O-)$ where $R^3$ is connected to the O atom in $R^2$.

6. The non-crosslinked silicon polyether composition of claim 1 wherein:

$R^2$ and $R^{14}$ are polyvalent linear or branched unsaturated or saturated hydrocarbon radicals optionally containing heteroatoms and hydroxyl groups subject to the limitation that the valency of $R^2$ and $R^{14}$ is at least two and contains from 1 to about 20 carbon atoms;

$R^{30}$ is a monovalent saturated or unsaturated hydrocarbon radical having from 1 to about 10 carbon atoms;

$R^4, R^5, R^6, R^{11}, R^{12}, R^{13}, R^{15}, R^{16}, R^{19}, R^{20}, R^{21}, R^{22}, R^{23}, R^{24}, R^{26}, R^{27}$, and, $R^{28}$ are each independently selected from the group of monovalent hydrocarbon radicals having from 1 to about 5 carbon atoms or $OR^{31}$, and $R^7, R^8$ and $R^9$ are each independently selected from the group of monovalent hydrocarbon radicals having from 1 to 5 carbon atoms;

$R^{10}, R^{17}, R^{18}, R^{25}$ and $R^{29}$ are independently selected from the group of divalent hydrocarbon radicals having 2 to about 20 carbon atoms;

$R^{32}$ is a divalent hydrocarbon radical having from 2 to about 20 carbon atoms;

$R^{33}$ is a monovalent saturated or unsaturated hydrocarbon radical having from 1 to about 10 carbon atoms;

subscripts a, b and c are zero or positive subject to the limitation $0 < a+b+c \leq$ about 250;

subscript s is positive subject to the limitation $0 < s < 10$ and s is equal to the valency of $R^{14}$ minus 1.

7. The non-crosslinked silicon polyether composition of claim 1 wherein:

$R^2$ and $R^{14}$ are polyvalent linear or branched unsaturated or saturated hydrocarbon radicals optionally containing heteroatoms and hydroxyl groups subject to the limitation that the valency of $R^2$ and $R^{14}$ is at least two and contains from 1 to about 15 carbon atoms;

$R^{30}$ is a monovalent saturated or unsaturated hydrocarbon radical having from 1 to about 5 carbon atoms;

$R^4, R^5, R^6, R^{11}, R^{12}, R^{13}, R^{15}, R^{16}, R^{19}, R^{20}, R^{21}, R^{22}, R^{23}, R^{24}, R^{26}, R^{27}$, and, $R^{28}$ are each independently selected from the group of monovalent hydrocarbon radicals having from 1 to about 3 carbon atoms or $OR^{31}$ and $R^7, R^8$ and $R^9$ are each independently selected from the group of monovalent hydrocarbon radicals having from 1 to 3 carbon atoms;

$R^{10}, R^{17}, R^{18}, R^{25}$ and $R^{29}$ are K are independently selected from the group of divalent hydrocarbon radicals having 3 to about 10 carbon atoms;

$R^{32}$ is a divalent hydrocarbon radical having from 3 to about 10 carbon atoms;

$R^{33}$ is a monovalent saturated or unsaturated hydrocarbon radical having from 1 to about 5 carbon atoms;

subscripts a, b and c are zero or positive subject to the limitation $0 < a + b + c \leqq$ about 200;

subscript s is positive subject to the limitation $0 < s < 10$ and s is equal to the valency of $R^{14}-1$.

8. The non-crosslinked silicon polyether composition of claim 1 further comprising at leas one additive selected from the group consisting of coupling agents, silane coupling agents, curing aids, activators, retarders, accelerators, processing additives such as oils, plasticizers, tackifying resins, silicas, fillers, pigments, fatty acids, zinc oxide, waxes, antioxidants and antiozonants, peptizing agents, reinforcing materials, and carbon black.

* * * * *